(12) United States Patent
Kriel

(10) Patent No.: US 7,467,540 B2
(45) Date of Patent: Dec. 23, 2008

(54) ANALYSIS SYSTEMS AND METHODS

(75) Inventor: Wayne A. Kriel, Friendswood, TX (US)

(73) Assignee: SGS Societe Generale de Surveillance S.A. (CH)

( * ) Notice: Subject to any disclaimer, the term of this patent is extended or adjusted under 35 U.S.C. 154(b) by 111 days.

(21) Appl. No.: 11/543,411

(22) Filed: Oct. 5, 2006

(65) Prior Publication Data

US 2007/0089483 A1    Apr. 26, 2007

Related U.S. Application Data

(60) Provisional application No. 60/724,185, filed on Oct. 6, 2005.

(51) Int. Cl.
  G01N 1/00    (2006.01)
  G01N 1/22    (2006.01)
  G01N 30/02    (2006.01)
  G01N 33/22    (2006.01)

(52) U.S. Cl. .................... 73/23.41; 73/19.02; 73/19.05; 73/19.1; 73/19.11; 73/19.12

(58) Field of Classification Search ............... 73/19.02, 73/19.05, 19.1, 19.11, 19.12, 23.41
See application file for complete search history.

(56) References Cited

U.S. PATENT DOCUMENTS 4,409,814 A * 10/1983 Onuma et al. .............. 73/19.11

| | | |
|---|---|---|
| 5,235,843 A | 8/1993 | Langhorst |
| 5,400,657 A | 3/1995 | Kolpak et al. |
| 5,499,531 A | 3/1996 | Henderson .................. 73/64.45 |
| 5,889,202 A | 3/1999 | Alapati et al. .............. 73/64.45 |
| 6,164,308 A | 12/2000 | Butler |
| 2003/0136185 A1 | 7/2003 | Dutton et al. .............. 73/61.44 |
| 2005/0155906 A1 | 7/2005 | Wellington et al. |

FOREIGN PATENT DOCUMENTS

EP    0092975    11/1983

OTHER PUBLICATIONS

W.A. Kriel et al.; "Improved Gas Chromatographic Analysis of Reservoir Gas and Condensate Samples"; Proceedings of the 1993 SPE International Symposium on Oilfield Chemistry; New Orleans, Louisiana, USA; Mar. 2-5, 1993; pp. 397-411.

Notification of Transmittal of the International Search Report and the Written Opinion of the International Searching Authority (form PCT/IS/220) and the International Search Report and Written Opinion of the International Searching Authority issued in counterpart PCT/US2006/038905; Jan. 18, 2007; 14 pages.

International Preliminary Report on Patentability under Chapter 11 issued in counterpart International Application No. PCT/US2006/038905; Jan. 16, 2008; 15 pages.

* cited by examiner

Primary Examiner—Daniel S Larkin
(74) Attorney, Agent, or Firm—Fish & Richardson P.C.

(57) ABSTRACT

A method of analyzing a composition including live crude includes separating the composition into a vapor phase and a liquid phase. A composition of the vapor phase is determined with a gas chromatograph. At least a portion of the liquid phase is deposited in a vessel, and a headspace vapor phase is collected from the vessel. A composition of the headspace vapor is determined with the gas chromatograph.

30 Claims, 3 Drawing Sheets

ANALYSIS SYSTEMS AND METHODS

The present application claims benefit of U.S. Provisional Application No. 60/724,185, filed Oct. 6, 2005, the disclosure of which is hereby incorporated by reference.

BACKGROUND

This disclosure relates to analyzing pressurized test samples, including hydrocarbons and reservoir fluids, such as live (pressurized) crude oil.

There are often instances where it is desired to determine the composition of a fluid that contains both liquid and vapor phases. For example, in the oil and gas production context, live crude is analyzed for allocation purposes, such as to determine gas to oil ratios, fluid shrinkage and compositional analysis. These fluids are typically produced at elevated pressures and temperatures. However, at atmospheric conditions, a gaseous or vapor portion of the fluid is released. It is typically infeasible to maintain the equipment for analyzing both liquid and vapor phases at the production site. Testing the live crude remote from the production site has certain disadvantages. Therefore, there is a need to remedy or lessen these disadvantages.

SUMMARY

In general terms, the concepts described herein encompass systems and methods for analyzing a substance that contains both liquid and vapor phases, including samples of hydrocarbons and reservoir fluids, such as live crude oil.

One aspect encompasses a method of analyzing a substance. In the method, the composition is separated into a vapor phase and a liquid phase. A composition of the vapor phase is determined with a gas chromatograph. At least a portion of the liquid phase is deposited in a vessel. At least a portion of the liquid phase is collected from the vessel. A composition of the liquid's headspace vapor is also determined with the gas chromatograph.

Another aspect encompasses a system for analyzing a composition. The system includes a phase separator adapted to separate the composition into a vapor and a liquid phase. A gas chromatograph is adapted to receive at least a portion of the vapor phase and perform a compositional analysis on the vapor phase. A container is adapted to receive at least a portion of the liquid phase and contain a headspace vapor therein. An inlet coupled to the gas chromatograph is adapted to withdraw at least a portion of the headspace vapor from the container and into the gas chromatograph. The gas chromatograph is adapted to receive at least a portion of the headspace vapor and perform a compositional analysis on the headspace vapor.

Another aspect encompasses a method of analyzing live crude. In the method a sample of the live crude is collected from a production site. A vapor phase of the composition is analyzed with a gas chromatograph residing at the production site. A liquid phase of the composition is analyzed with the gas chromatograph.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
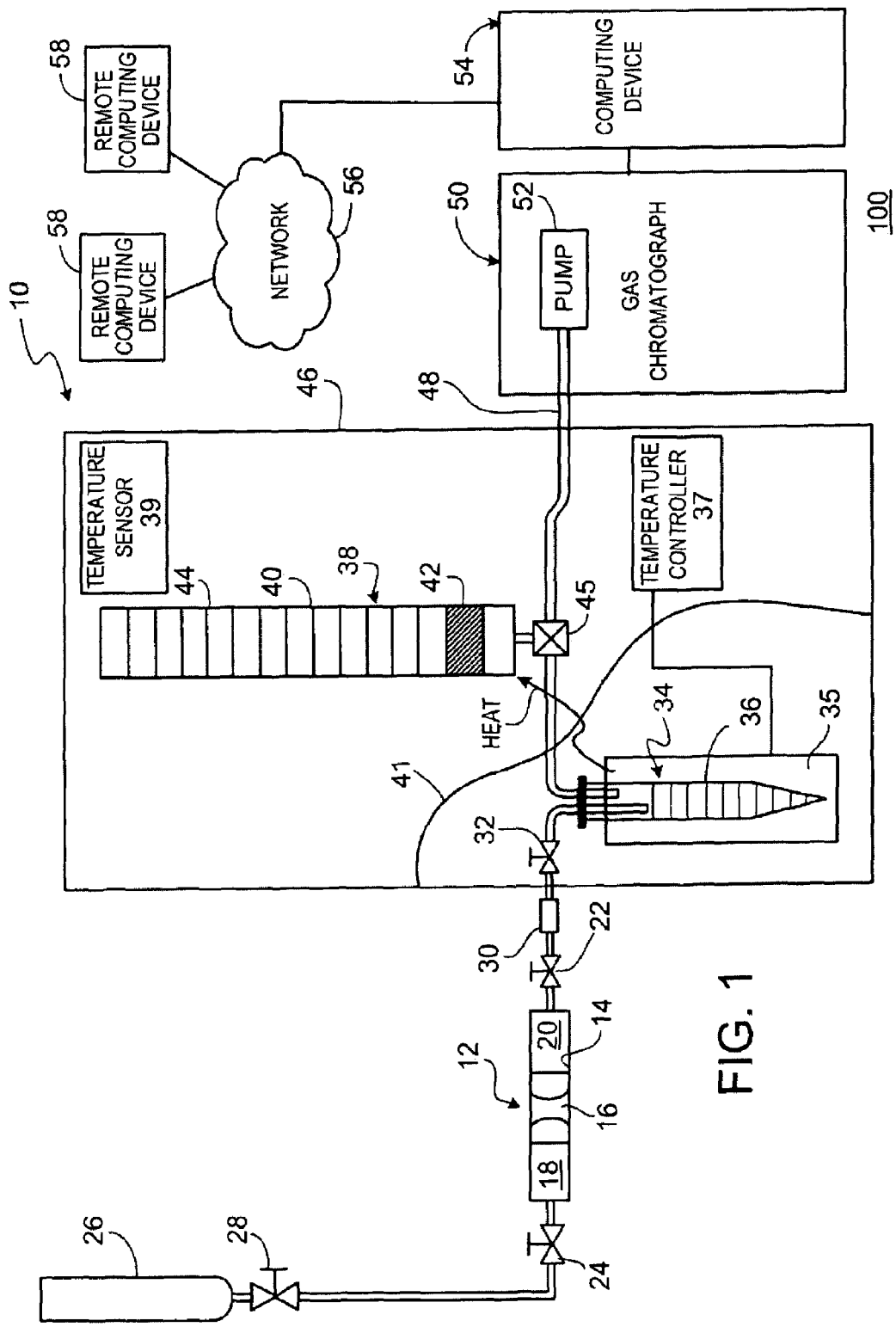
FIG. 1 is a schematic of an illustrative analysis system constructed in accordance with the concepts described herein.

Referring first to FIG. 1, an illustrative analysis system 10 is depicted. The illustrative analysis system 10 operates to receive a fluid sample of a substance, such as live crude oil, and perform a compositional analysis of all or part of the fluid sample. The illustrative analysis system 10 can also operate to determine one or more of the amount of vapor, the amount of liquid phases, or the amount of solid of the fluid sample. Of note, although live crude oil is referenced in numerous locations throughout the description, the concepts described herein are applicable to analyzing other substances. Also, the substance need not be fluid or entirely fluid.

The illustrative analysis system 10 includes a sample vessel 12 operable to receive the fluid sample, and subsequently release the fluid sample into the remainder of the system 10. In certain embodiments, the sample vessel 12 may be removed from the system 10 and transported to collect the fluid sample. For example, the sample vessel 12 may be carried by an operator from the system 10 to a location where the sample will be collected, the sample collected, and the sample vessel 12 returned to the system 10. This eliminates the need to transfer the fluid sample between multiple vessels, such as between the location where the sample is collected and an intermediate sample vessel and from an intermediate sample vessel and the sample vessel 12. In other embodiments, the sample vessel 12 may remain connected to the remainder of the system 10 throughout operation and the sample collected and deposited in the sample vessel 12, such as via an intermediate sample vessel.

The illustrative sample vessel 12 of FIG. 1 internally defines an elongate cavity 14 that sealingly receives a piston 16. The piston 16 divides the elongate cavity 14 into two distinct chambers, a drive fluid chamber 18 and a sample chamber 20. The sample chamber 20 is operable to receive the fluid sample through a valve (referred to herein as "sample valve 22"). After receiving the fluid sample, the sample valve 22 may be closed to retain the fluid sample in the sample chamber 20.

In certain embodiments, the sample vessel 12 may be configured to operate as a pycnometer. To this end, the maximum volume of the sample chamber 20 is precisely calibrated for pressure and temperature. Additionally, the "dry" weight of the sample vessel 12 is precisely known. The volume of the fluid sample, thus, may be determined by adjusting the maximum volume of the sample chamber 20 for the temperature and pressure of the fluid sample therein. The weight of the fluid sample may be determined by weighing the sample vessel 12 containing the fluid sample, and subtracting the dry weight of the sample vessel 12. The density of the fluid sample may be determined by dividing the determined volume by the determined weight.

In certain embodiments, the size of the sample vessel 12 may be selected to facilitate handling by the operator. A smaller vessel is more easily manipulated and carried by the operator. In one instance, the sample vessel 12 has an internal volume of 10 cc when calibrated at 10 MPa and 20° C. and is constructed from 316 stainless steel. To facilitate removal and return of the sample vessel 12 to the system 10, an outlet of the sample vessel 12 may be coupled to a quick release connection 30 that allows easy installation and removal of the sample vessel 12 from the remainder of the system 10. In certain embodiments, low dead volume fittings are used in one or more locations of the system 10, for example, the connections with the sample vessel 12.

As noted above, the sample vessel 12 includes a piston 16 that divides the elongate cavity 14 into two distinct chambers, a drive fluid chamber 18 and a sample chamber 20. The sample vessel 12 may further include a valve (referred to herein as "drive valve 24") provided in communication with the drive fluid chamber 18. With the drive valve 24 open, receiving the fluid sample in the sample chamber 20 drives the piston 16 in the elongate cavity 14 to expand the sample chamber 20 and reduce the drive fluid chamber 18. A drive fluid may be introduced through the drive valve 24 to pressurize the drive fluid chamber 18. Pressure in the drive fluid chamber 18 exerts pressure, via the piston 16, on the fluid sample in the sample chamber 20. When the sample valve 22 is opened, the pressure in the sample chamber 20 drops. Pressure in the drive fluid chamber 18 drives the piston 16 to reduce the sample chamber 20 and drive the fluid sample out of the sample vessel 12. In some instances, for example where the fluid sample is live crude under pressure, the fluid sample may become two phase (i.e. vapor and liquid) when the sample valve 22 is opened and pressure within the sample chamber 20 drops. The heavier liquid phase of the fluid sample then accumulates about the bottom of the sample chamber 20, and the vapor phase of the fluid sample at the top of the sample chamber 20. Movement of the piston 16 ensures that both the vapor and liquid phase of the fluid sample are expelled into the remainder of the system 10.

The drive fluid may be sourced from a number of different sources. In the illustrative system 10, the drive fluid is pressurized gas stored in a canister 26. The outlet of the canister 26 may be sized or a restriction may be provided about the outlet of the canister 26 (FIG. 1 depicts a metering valve, referred to herein as "canister valve 28") to meter the flow from the canister 26. In certain embodiments, the canister 26 is a standard 12-gram $CO_2$ cartridge, such as those used with $CO_2$ powered guns. The standard 12-gram $CO_2$ cartridge can apply approximately 1200 psig driving pressure to the drive fluid chamber 18.

Although described above as using a drive fluid to evacuate the sample chamber 20, the fluid sample may be evacuated from the sample chamber 20 in other manners. For example, a mechanical or electromechanical system, such as a motor and a gear train or screw drive, may be used to move the piston 16.

The outlet of the sample vessel 12 communicates with a restriction 32, such as a metering valve, that causes the fluid sample released from the sample vessel 12 to flash into a vapor phase in a liquid phase. Although depicted in FIG. 1 as a separate metering valve, the restriction 32 may be other restrictions in the system. For example, in some instances the restriction 32 may be the valve 22 associated with the sample vessel 12 or another variable or fixed orifice in the system 10.

The liquid phase is collected in a liquid accumulator 34 and the vapor phase continues on through the system 10. In certain embodiments, the liquid accumulator 34 can be cooled by a cooling element 35 to facilitate and/or increase condensation of liquid in the liquid accumulator 34. In the example of FIG. 1, the cooling element 35 includes a Peltier effect device configured to carry (e.g. by aluminum holder) and conductively transfer heat with the liquid accumulator 34. In other embodiments, the cooling element 35 can be different, for example, the cooling element 35 can use an electrical cooler, a chemical cooler or another device configured for one or more modes of heat transfer. In some instances, the cooling element 35 can be controlled by a temperature controller 37 to maintain the contents of the liquid accumulator 34 at a substantially constant temperature.

In certain embodiments, the liquid accumulator 34 includes graduations 36 that enable visual determination of the volume collected in the liquid accumulator 34. The "dry" weight of the liquid accumulator 34 prior to receipt of the liquid phase may be precisely measured. The weight of the liquid phase can then be determined by measuring the weight of the liquid accumulator 34 after receipt of the liquid phase and subtracting the dry weight of the liquid accumulator 34. The density of the liquid phase can be determined via a handheld densitometer. The volume of the liquid phase collected in the liquid accumulator 34 can be determined with reference to the graduation 36 or by dividing the weight of the liquid phase in the accumulator 34 by the density determined via the handheld densitometer.

In an example where the fluid sample includes live crude, the volumetric shrink can be determined by comparing the volume of liquid phase contained in the liquid accumulator 34 to the maximum volume, adjusted for pressure and temperature, of the fluid sample in the sample vessel 12.

In certain embodiments, the liquid accumulator 34 is a centrifuge tube that can be removed from the system 10 and directly, without transferring the fluid to another vessel, inserted into a centrifuge device (not shown). In an example where the fluid sample is live crude, the liquid phase may include oil, water and entrained solids. Centrifuging the liquid phase separates the oil, water, and solids and enables measurement, for example visually using the graduations 36, of the volume of oil, water and solids. The volume and weight of liquid phase in the liquid accumulator 34 can be corrected for water and sediment recovered during the centrifuging process without the need of taking another fluid sample.

The vapor phase is communicated to a gas meter 38 that operates to measure the amount of the vapor phase collected. The gas meter 38, liquid accumulator 34 and restriction 32 can be contained in a common housing 46. In certain embodiments, the gas meter 38 is a floating piston gas meter having a graduated cylinder 40 that sealingly receives a piston 42. In some instances, the piston 42 can additionally or alternatively be coupled to a graduated shaft (e.g. a plunger handle) extending from the cylinder 40. Receipt of the vapor phase in the graduated cylinder 40 displaces the piston 42, and the volume of the vapor phase can be visually determined from the graduations 44 on the cylinder 40 (or on the shaft, if so provided). The cylinder 40 can be purged, via a valve 45, prior to receipt of the vapor phase to ensure an accurate measurement.

The temperature and pressure of the vapor in the gas meter 38 are monitored, so that the volume determined with the gas meter 38 can be corrected to standard conditions. In certain embodiments, a temperature sensor 39, for example a digital thermometer, can be provided to measure the temperature in the gas meter 38. Additionally, in some instances, the temperature of the vapor in the gas meter 38 can be regulated. In the configuration of FIG. 1, the gas meter 38 is heated by the heat output from the cooling element 35 (here, a Peltier effect device) to decrease formation of condensation in the gas meter 38. Other embodiments may use a separate heating element, for example, an electrical heating element, Peltier effect device, chemical heater or another device, to heat the gas meter 38 and, in some instances, that heating element can be controlled by the temperature controller 37 or another temperature controller to maintain the contents of the gas meter 38 at a substantially constant temperature. Further, an insulative barrier 41 can be provided to substantially thermally isolate a portion of the system 10 from the remainder of the system 10. In certain embodiments, the liquid accumulator 34, restriction 32 and related conduits are thermally isolated from the gas meter 38 to reduce communication of heat output from the cooling element 35 (or separate heating element if so provided) to the liquid phase of the sample.

The gas meter 38 may contain an internal mixer. In one instance, the internal mixer is a magnetic mixer. The internal magnetic mixer may be operated during or at the end of each vapor collection cycle to ensure that the vapor containing the gas meter is well mixed and of a uniform composition.

The housing 46 may contain one or more lights to facilitate operation of the system 10. For example, the lights may illuminate the liquid accumulator 34 and/or gas meter 38 to aid in viewing the respective fluid levels of each.

The vapor phase of the fluid sample is delivered to a gas chromatograph 50. In certain embodiments, a conduit 48 extends between an outlet of the gas meter 38 and the gas chromatograph 50. Thus, the vapor phase is communicated directly to the gas chromatograph 50. The conduit 48 may be heated to reduce and/or minimize formation of condensate as the vapor phase is communicated to the gas chromatograph 50. A pump 52 may be provided to draw vapor from the gas meter 38 into the gas chromatograph 50. In certain embodiments, the pump 52 is provided within or as a component of the gas chromatograph 50. However, in other instances, the pump 52 may be provided outside of the gas chromatograph 50. The pump 52 is operable to draw a portion of the vapor phase into the gas chromatograph 50, and the gas chromatograph is operable to perform gas chromatography analysis of the vapor phase and output data indicating the composition of the vapor phase. In one instance, the gas chromatograph 50 is a Micro GC manufactured by Varian, Inc. The Micro GC is a small gas chromatograph that is designed to be easily transported and includes an internal pump that can operate as pump 52.

In certain embodiments, the gas chromatograph 50 can communicate with a computing device 54, such as a personal computer, a hand held computer, or other computing device, to enable viewing, analysis and manipulation of the data output from the gas chromatograph 50 or other components of the system 10. In certain embodiments, the computing device 54 is linked to a network 56 that allows remote computing devices 58 to communicate with the computing device 54 and in some instances remotely operate the gas chromatograph 50. In certain embodiments, the computing device 54 can enable a remote party to communicate with the operator of the system 10 to provide the operator instruction on operating the system 10.

In certain embodiments, the composition of the liquid phase can be analyzed with the gas chromatograph 50. Typically, gas chromatographs can only analyze vapor or gas samples without additionally using an analytical separation column. However by utilizing a headspace technique, a gas chromatograph can be used to analyze the composition of the liquid phase. In general, in a headspace technique, a portion of the liquid phase is vaporized in the headspace of a sample vial and the vapor from the headspace of the sample vial is analyzed with a gas chromatograph 50. In addition to enabling use of the gas chromatograph to analyze a both the composition of the liquid and gas phases, the headspace technique eliminates the need for temperature programming, and back flush valuing to elute or eliminate the build up of higher boiling components.

Figure 2:
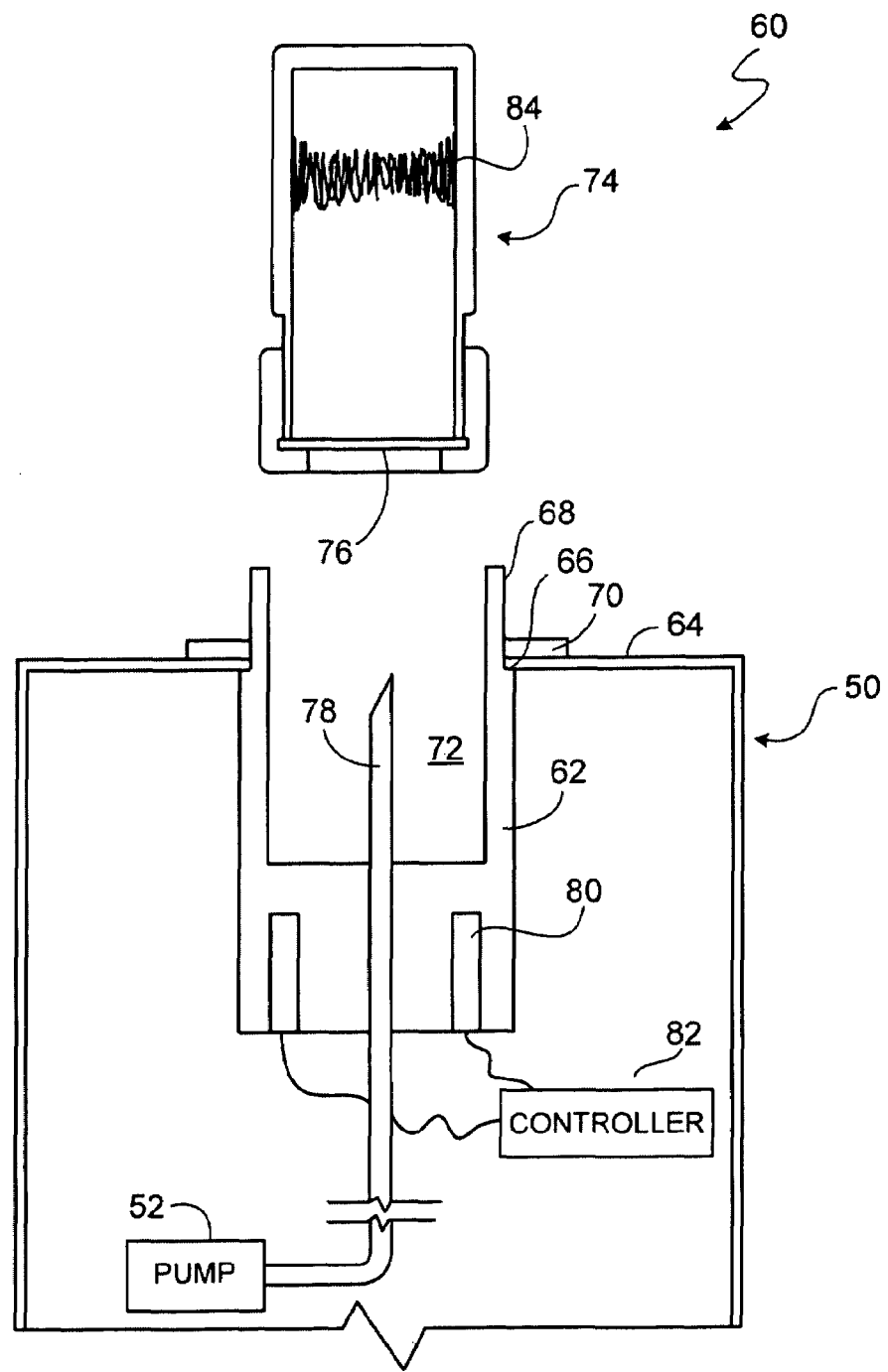
FIG. 2 is a schematic of an illustrative system for performing headspace analysis with a gas chromatograph in accordance with the concepts described herein.

An illustrative system 60 for performing the headspace technique with the gas chromatograph 50 is depicted in FIG. 2. The illustrative headspace system 60 includes an adapter body 62 adapted to couple to the gas chromatograph 50. In the illustrative embodiment of FIG. 2, the adapter body 62 is received substantially within a housing 64 of the gas chromatograph 50. A threaded stub 68 of the body 62 extends through the housing 64 and threadingly receives a nut 70. The nut 70 captures the housing 64 against a shoulder 66 of the adapter body 62, thus affixing the adapter body 62 to the housing 64. In other embodiments, the adapter body 62 can be configured to couple to the gas chromatograph 50 in a different manner or can reside apart from the gas chromatograph 50.

The body 62 defines an interior cavity 72 sized to receive a sample vial 74. The sample vial 74 includes a septum 76 substantially sealing its open end. In certain embodiments, the septum is made of silicon. The body 62 supports a sampling needle 78 in the cavity 72 positioned to pierce the septum 76 and allow the sampling needle 78 to withdraw vapor from within the sample vial 74 when the sample vial 74 is received by the adapter body 62. In certain embodiments, the sampling needle 78 is positioned to withdraw from a central area within the sampling vial 74. The body 62 further includes a one or more heating elements 80 operated by a controller 82. The heating elements 78 heat the adapter body 62, which in turn, heats the sample vial 74 and its contents.

In operation, a sample of the liquid phase is placed in the sample vial 74. In certain embodiments, the liquid phase, such as oil, is applied as a thin film 84 on the interior of the sample vial 74. In one instance, the amount of the liquid phase is approximately 5 ul and the sample vial is approximately 25 cc. The heating elements 78 are operated to heat the sample and cause a portion of the sample to vaporize (i.e. form a vapor in the headspace of the sample vial 74). The controller 82 enables the heating elements 80 to be controlled to attain a desired amount of heating to vaporize the liquid phase.

The sampling needle 78 is coupled to the pump 52. After a period of time to allow the sample to equilibrate, in one instance approximately five minutes, the pump 52 is operated to withdraw a sample of the headspace vapor into the analysis portion of the gas chromatograph 50. Thereafter, the gas chromatograph 50 can be operated to determine a composition of the headspace vapor, which is representative of the composition of the liquid phase. In certain embodiments the detection is performed by thermal conductivity. The resulting peak areas are converted to a weight percent basis via external standard quantification. In certain embodiments, the headspace technique described above can also or alternatively be performed on solids. For example, the headspace technique can be performed on soil samples deposited in the sample vial 74.

The composition of the liquid sample may then be analyzed as follows. A small portion of the liquid sample is analyzed for average molecular weight. For example, approximately 0.2 g can be analyzed via a benzene freezing point method to determine the molecular weight. The molecular weight is then mathematically combined with the weight percent compositions derived from the headspace technique described above to produce a compositional analysis on a mole percent basis. The individual mole percent of each individual component up to isopentane is reported by this method. Hexanes through pentadecane are grouped as individual pseudo-components using the normal paraffins of each series as the pseudo-component cut offs. The resulting pseudo-components are converted to weight percent in a similar fashion to that described above, while the mole percent of hexadecane and above is calculated from material and mole balance calculations. The resulting compositional analysis may thus report the liquid compositions expressed in weight percent, volume percent and mole percent.

The composition of the liquid sample may then be combined with the compositional analysis of the gas sample using standard practices to produce a "live fluid" composition. The live fluid composition can be used for computer model simulations to determine fluid phase behavior and thus fluid ownership or allocation. One or more of the calculations described above can be performed by a computer, such as computing device 54. The computing device 54 may incorporate dedicated software or generic software, e.g. a spreadsheet, that facilitates performing the calculations and/or recording and storing the resultant data.

Figure 3:
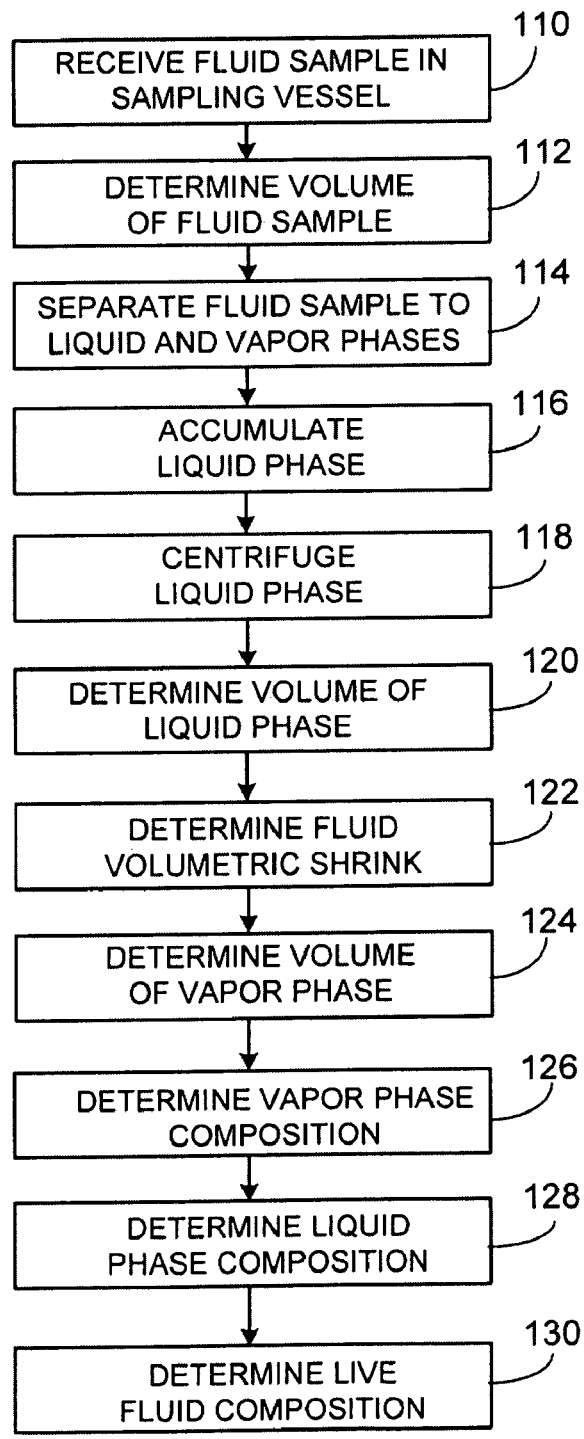
FIG. 3 is a flow diagram of an illustrative method in accordance with the concepts described herein.

An illustrative method of analyzing live crude enabled by the illustrative system 10 is described with reference to FIG. 3. In the illustrative method, a fluid sample is received in a sample vessel, such as sample vessel 12, at operation 110. The sample vessel can be evacuated prior to receiving the sample. In an example using the sample vessel 12, the piston 16 can be moved to reduce the volume of the sample chamber 20 by pressurizing the drive fluid chamber 18. In some instances, the sample vessel is detached from the remainder of the system and transported to the location at which the sample will be taken. The source of the sample can be purged, in some instances at least 100 ml is purged, prior to collecting the sample to reduce the likelihood of contamination in the sample. The fluid sample is then collected in a sample chamber of the sample vessel, and pressure is allowed to stabilize in the sample chamber. If the sample vessel is so configured, the sample vessel, and in some instances two or more sample vessels at a time, may be easily carried and handled by an operator.

At operation 112, the volume of the fluid sample in the sample vessel is determined. If the maximum volume of the sample chamber of the sample vessel is precisely known at a calibrated pressure and temperature, the volume of the sample may be determined by extrapolating the volume of the sample chamber 20 to the pressure and temperature of the sample. The weight of the sample may be determined by weighing the sample vessel including the fluid sample in the sample chamber and subtracting the dry weight of the sample vessel.

At operation 114 the fluid sample is separated into liquid and vapor phases. In some instances, the fluid sample is separated into liquid and vapor phases by flashing the fluid sample across a restriction. In an example using the sample vessel 12, the sample vessel 12 may be returned to the system 10, and pressure applied into the drive fluid chamber 18. Pressure may be maintained on the sample and the sample fluid fully evacuated from the sample vessel as the volume of the sample chamber 20 is reduced while the fluid sample leaves the vessel. In some instances, the liquid and vapor phases can be released across the restriction at approximately 10 cc/second.

At operation 116, the liquid phase of the fluid sample is accumulated. In some instances, the liquid phase may be accumulated in a liquid accumulator that is also a centrifuge tube.

At operation 118, the liquid phase is centrifuged to separate oils, water and solids. If the liquid phase was accumulated in a centrifuge tube, the liquid accumulator may be directly transferred to a centrifuge to perform the centrifuging operation. If the liquid phase was not accumulated into a centrifuge tube, the contents of the accumulated liquid phase may be transferred to a centrifuge tube prior to the centrifuging operation.

At operation 120, the volume of the liquid phase is determined, for example, by reading graduations on the centrifuge or accumulator tube. The volume of the liquid phase can be corrected for water and solids, by subtracting the volume of the water and solids from the total volume in the centrifuge or accumulator tube. The weight of the liquid phase in the centrifuge or accumulator tube may be determined by weighing the centrifuge or accumulator tube with liquid phase sample and subtracting the dry weight of the centrifuge or accumulator tube. In some instances, the interior of the sample vessel and other components of the system can be wiped down with cleaning wipes, and the weight difference of the cleaning wipes before and after use can be added to the weight of the liquid phase determined from the centrifuge or accumulator tube to more accurately determine the total weight of the liquid phase.

At operation 122, the fluid volumetric shrink is determined. The volumetric shrink can be determined by comparing the volume of liquid phase contained in the liquid accumulator 34 to the maximum volume, adjusted for pressure and temperature, of the fluid sample in the sample vessel 12.

At operation 124, the volume of the vapor phase is determined. In one instance, the vapor phase is communicated to a gas meter 38 that operates to measure the amount of vapor phase collected.

At operation 126 the composition of the vapor phase can be determined. In one instance, the vapor phase is communicated to a gas chromatograph that performs chromatography on the vapor phase to determine its composition.

At operation 128, the composition of the liquid phase is determined. In one instance, the composition of the liquid phase is determined using a headspace technique and the same gas chromatograph used in determining the composition of the vapor phase.

At operation 130, using the composition of the vapor phase in the composition of the liquid phase, the composition of the live fluid can be determined.

Although described in a particular order, the operations described above may be performed in a different order. Additionally, one or more of the steps may be omitted, or additional steps may be added.

Although not necessary for the concepts described herein, using a gas chromatograph to analyze the composition of both the vapor and liquid phases can eliminate the additional equipment used in analyzing the liquid phase of the sample. In many cases, the additional equipment required to analyze the liquid phase is voluminous and cannot be maintained in small lab facilities. The equipment is also not feasibly transported. As a result, the equipment necessary to analyze the liquid phase of the sample, as well as the remainder of the equipment needed to analyze the sample, are maintained in centralized testing facilities in various locations about the world. A sample may travel tens or hundreds of miles from the location at which it is taken to the centralized testing facility.

For example, although offshore platforms typically maintain a small lab, the space on the platform does not allow the equipment necessary to analyze the liquid phase. Therefore, a sample taken on the offshore platform would normally be transported to an onshore testing facility. Similarly, it is not practical to maintain the voluminous analysis equipment at remote onshore sampling sites, such as sites in rural areas. Depending on the location of the offshore platform or rural onshore sampling site, the sample may travel tens or hundreds of miles to reach the testing facility. This travel introduces a many hour lag between the time the sample is taken and the time the analysis can be performed. This time lag discourages frequent testing and hinders retesting. The travel increases the likelihood that the sample will become compromised and or contaminated, and introduces additional expenses in travel and time into the costs of analysis. If a sample is contaminated or fouled, during collection, transport or otherwise, it will not be discovered until the sample has traveled the many miles to reach the centralized testing facility. Another sample must then be taken and transported to the centralized testing facility or the analysis forgone.

In contrast, a single gas chromatograph, and especially a gas chromatograph configured for portability, is smaller, easily transported and can be maintained in a small lab facility. Thus, the analysis system 10 can be maintained at or near the sampling location. For example, the analysis system can be maintained on an offshore platform 100. Maintaining the analysis equipment at the sampling location enables frequent testing and eliminates the time delay and costs associated with transporting the sample. If it is not feasible to maintain the entire analysis equipment at the sampling location, the analysis equipment can be transported to the sampling location. Having the analysis equipment near the sampling location enables quick retesting if the sample is contaminated during collection, transport or otherwise. In some instances, the entire system may fit into two suitcases that can be handled by an operator without equipment, such as a hoist or fork truck.

Although not necessary for the concepts described herein, the system may be a continuous or near continuous system that operates on a single amount of the sample to analyze the composition and other characteristics with few or no transfers of the sample between vessels. Systems that are not continuous or near continuous may be a series of disparate tests that require separate amounts of the sample for each analysis performed and multiple transfers between vessels. Separate amounts of sample for each and analysis performed inherently requires a larger volume of initial sample to pull the intermediate sample amounts from. Furthermore, there are losses of the sample as residue is left on the various containers between which the samples are transferred.

In contrast, in the system described above, the sample collected in the sample vessel is communicated continuously through the system for analysis with only one transfer stemming from the transfer into the headspace vial. If so configured, other transfers are not necessary. For example, collecting the sample to be analyzed in the sample vessel that also operates to evacuate the sample into the system and as a pycnometer eliminates multiple transfers, i.e. between an intermediate sample vessel and the sample vessel and between the sample vessel and a pycnometer. In another example, accumulating the liquid phase in a centrifuge tube eliminates the need to transfer between an accumulator and a centrifuge tube. In yet another example, the liberated gas phase is taken from the liquid accumulator and communicated directly to the gas chromatograph without using a transfer container or vial. By operating on a single amount of the sample to analyze the composition and other characteristics, the system is inherently more conservative of the amount of the sample used. Likewise, in a system that is located at or near the sampling location, little or no additional sample need to be collected for retesting purposes because additional sample can be quickly and easily collected. Therefore, a smaller amount of sample can be collected, enabling use of a smaller sample vessel that is easier to transport between the sampling location and the remainder of the system. Additionally use of a smaller sample vessel contributes to the reduced size and ease of transportation of the system. Also, because the entire sample in the sample vessel is used for analysis, no pumps are required to extract small amounts of the sample for use in a series of disparate tests.

A number of embodiments of the invention have been described. Nevertheless, it will be understood that various modifications may be made without departing from the spirit and scope of the invention. Accordingly, other embodiments are within the scope of the following claims.

What is claimed is:

1. A method of analyzing a substance, comprising:
separating the substance into a vapor phase and a liquid phase;
determining a composition of the vapor phase with a gas chromatograph;
depositing at least a portion of the liquid phase in a vessel;
collecting a headspace vapor produced from the liquid phase in the vessel; and
determining a composition of the headspace vapor with the gas chromatograph.

2. The method of claim 1 further comprising heating the liquid phase in the vessel to produce the headspace vapor.

3. The method of claim 1 wherein collecting a headspace vapor phase from the vessel comprises sealingly coupling an inlet of the gas chromatograph to the vessel and drawing the headspace vapor into the gas chromatograph.

4. The method of claim 3 wherein drawing the headspace vapor into the gas chromatograph comprises operating a suction pump associated with the gas chromatograph.

5. The method of claim 1 further comprising collecting a sample of the substance in a pycnometer, and wherein the step of separating the substance into a vapor phase and a liquid phase is performed on the substance collected in the pycnometer.

6. The method of claim 5 wherein the method further comprises:
determining a volume of the sample using the pycnometer;
measuring a volume of the separated liquid phase; and
determining a volumetric shrink as a function of the volume of the sample and the volume of the liquid phase.

7. The method of claim 1 wherein separating the substance into a vapor phase and a liquid phase comprises flashing the substance and collecting the liquid phase in a centrifuge vial.

8. The method of claim 7 wherein the substance comprises live crude and the method further comprises centrifuging the liquid phase in the centrifuge vial to separate oil, water and sediment in the liquid phase, and determining a volume of the oil.

9. The method of claim 1 wherein the vapor phase is communicated directly from a restriction to the gas chromatograph, the restriction causing the phase separation.

10. The method of claim 1 wherein determining a composition of the headspace vapor with the gas chromatograph is performed on an offshore platform.

11. The method of claim 1 further comprising after separating the vapor phase and the liquid phase, heating the vapor phase to reduce condensation thereof and cooling the liquid phase to facilitate condensation thereof.

12. A system for analyzing a composition, comprising:
a phase separator adapted to separate the composition into a vapor phase and a liquid phase;
a gas chromatograph adapted to receive at least a portion of the vapor phase and perform a compositional analysis on the vapor phase;
a container adapted to receive at least a portion of the liquid phase and contain a headspace vapor produced from the liquid phase therein; and
an inlet coupled to the gas chromatograph adapted to withdraw at least a portion of the headspace vapor from the container and into the gas chromatograph, the gas chromatograph adapted to receive at least a portion of the headspace vapor and perform a compositional analysis on the headspace vapor.

13. The system of claim 12 further comprising a heater adapted to heat the liquid phase in the container to produce a headspace vapor.

14. The system of claim 12 further comprising a pump associated with the gas chromatograph adapted to pump at least a portion of the headspace vapor into the gas chromatograph.

15. The system of claim 12 wherein the phase separator separates the composition by pressure differential.

16. The system of claim 12 further comprising a sample vessel adapted for transporting a sample of the composition between a source of the composition and the phase separator, the sample vessel adapted to operate as a pycnometer.

17. The system of claim 12 further comprising a centrifuge tube in fluid communication with the phase separator and adapted to accumulate the liquid phase therein.

18. The system of claim 17 further comprising a cooler adapted to cool the centrifuge tube while it is operating to accumulate the liquid phase.

19. The system of claim 12 residing on an offshore platform.

20. A method of analyzing live crude, comprising:
collecting a sample of the live crude from a production site;
separating the sample into a vapor phase and a liquid phase;
analyzing the vapor phase of the sample with a gas chromatograph residing at the production site; and
analyzing the liquid phase of the sample with the gas chromatograph.

21. The method of claim 20 wherein the production site is an offshore platform.

22. The method of claim 20 wherein analyzing a liquid phase of the sample with the gas chromatograph comprises performing a headspace vapor technique.

23. A method of analyzing a substance, comprising:
collecting a sample of the substance in a pycnometer;
separating the sample of the substance into a vapor phase and a liquid phase;
determining a composition of the vapor phase with a gas chromatograph;
depositing at least a portion of the liquid phase in a vessel;
collecting a headspace vapor from the vessel;
determining a composition of the headspace vapor with the gas chromatograph;
determining a volume of the sample using the pycnometer;
measuring a volume of the separated liquid phase; and
determining a volumetric shrink as a function of the volume of the sample and the volume of the liquid phase.

24. A method of analyzing a substance, comprising:
flashing the substance into a vapor phase and a liquid phase;
collecting the liquid phase in a centrifuge vial;
determining a composition of the vapor phase with a gas chromatograph;
depositing at least a portion of the liquid phase in a vessel;
collecting a headspace vapor from the vessel; and
determining a composition of the headspace vapor with the gas chromatograph.

25. The method of claim 24 wherein the substance comprises live crude and the method further comprises:
centrifuging the liquid phase in the centrifuge vial to separate oil, water and sediment in the liquid phase; and
determining a volume of the oil.

26. The method of claim 24 wherein depositing at least a portion of the liquid phase in a vessel comprises keeping at least a portion of the liquid phase in the centrifuge vial.

27. A method of analyzing a substance, comprising:
separating, by a restriction, the substance into a vapor phase and a liquid phase;
communicating the vapor phase directly to a gas chromatograph;
determining a composition of the vapor phase with the gas chromatograph;
depositing at least a portion of the liquid phase in a vessel;
collecting a headspace vapor from the vessel; and
determining a composition of the headspace vapor with the gas chromatograph.

28. A system for analyzing a composition, comprising:
a phase separator adapted to separate the composition into a vapor phase and a liquid phase by pressure differential;
a gas chromatograph adapted to receive at least a portion of the vapor phase and perform a compositional analysis on the vapor phase;
a container adapted to receive at least a portion of the liquid phase and contain a headspace vapor therein;
an inlet coupled to the gas chromatograph adapted to withdraw at least a portion of the headspace vapor from the container and into the gas chromatograph, the gas chromatograph adapted to receive at least a portion of the headspace vapor and perform a compositional analysis on the headspace vapor.

29. A system for analyzing a composition, comprising:
a phase separator adapted to separate the composition into a vapor phase and a liquid phase;
a centrifuge tube in fluid communication with the phase separator and adapted to accumulate the liquid phase therein;
a gas chromatograph adapted to receive at least a portion of the vapor phase and perform a compositional analysis on the vapor phase;
a container adapted to receive at least a portion of the liquid phase and contain a headspace vapor therein; and
an inlet coupled to the gas chromatograph adapted to withdraw at least a portion of the headspace vapor from the container and into the gas chromatograph, the gas chromatograph adapted to receive at least a portion of the headspace vapor and perform a compositional analysis on the headspace vapor.

30. The system of claim 29 further comprising a cooler adapted to cool the centrifuge tube while it is operating to accumulate the liquid phase.

* * * * *